United States Patent [19]
Royalty et al.

[11] Patent Number: 5,498,228
[45] Date of Patent: Mar. 12, 1996

[54] ELECTROMAGNETIC BI-VENTRICULAR ASSIST DEVICE

[75] Inventors: John W. Royalty, 6151 N. Suncoast Blvd., Suite 1F, Crystal River, Fla. 34428; James M. B. Royalty, Carrollton, Tex.; Lawrence A. Lynn, Worthington, Ohio

[73] Assignee: John W. Royalty, Crystal River, Fla.

[21] Appl. No.: 287,254

[22] Filed: Aug. 8, 1994

[51] Int. Cl.[6] .................................................. A61M 1/12
[52] U.S. Cl. ...................... 600/16; 607/3; 623/3
[58] Field of Search ........................ 600/16, 17; 607/3; 623/3

[56] References Cited

U.S. PATENT DOCUMENTS

| | | |
|---|---|---|
| 3,633,217 | 1/1972 | Lance . |
| 3,733,616 | 5/1973 | Willis . |
| 4,176,411 | 12/1979 | Runge . |
| 4,185,617 | 1/1980 | Hutchins . |
| 4,302,854 | 12/1981 | Runge . |
| 4,621,617 | 11/1986 | Sharma . |
| 4,809,676 | 3/1989 | Freeman .......................... 623/3 |
| 4,869,656 | 9/1989 | Della Sala .................... 623/3 |
| 5,205,810 | 4/1993 | Guiraudon et al. ............ 623/3 |

OTHER PUBLICATIONS

Schuder et al, "Ultrahigh Power Electromagnetic Energy Transport Into the Body", Amer. Soc. Artif. Int. Organs, vol. XVII, 1971, pp. 406–410.

Schreiner, et al, "Transactions American Society for Artificial Internal Organs", Amer. Soc. Artif. Int. Organs, vol. VI, 1960, pp. 292–294.

Primary Examiner—William E. Kamm
Assistant Examiner—Marianne Parker
Attorney, Agent, or Firm—Cushman Darby & Cushman

[57] ABSTRACT

A device and method for assisting ventricular output in a human heart by compressing the heart. In the method, an electrocardiogram is generated as a function of the electrical activity of the heart, and an electromagnetic field is generated as a function of the electrocardiogram. A magnetic mat is moved towards the vertebral body to compress the heart therebetween in response to application of the electromagnetic field thereto. The device includes a transducer and control circuit to regulate the compressive force applied to the heart.

19 Claims, 3 Drawing Sheets

5,498,228

ELECTROMAGNETIC BI-VENTRICULAR ASSIST DEVICE

BACKGROUND OF THE INVENTION

1. Field of the Invention

This invention relates to cardiac assist devices, and more particularly, to a device and method for assisting ventricular output in the human heart.

2. Description of the Related Art

During the aging process, weakened or ineffective cardiac muscles may inhibit the cardiac pumping function from either the right, left, or both ventricles. When the pumping activity of the heart cannot meet the body's demands, systemic shock and subsequent organ dysfunction (such as pulmonary edema and renal failure) can result. Weakened heart muscles can also result in an over distended, dilated myocardium, which can have a detrimental effect on the electrical conduction and overall mechanical performance of the heart.

Advances in medical science have attempted to overcome these problems by replacing an impaired heart via heart transplants, or with devices such as artificial hearts. However, heart transplants are difficult to obtain since there is a limited donor supply. Moreover, artificial hearts have proved not entirely effective in duplicating cardiac contractions, are extremely expensive, and are known to be rejected by the human body.

Therefore, rather than replacing the heart, various arrangements have been proposed to assist right and left ventricular output of the existing impaired heart. For example, a number of arrangements are suggested in U.S. Pat. No. 4,621,617 to Sharma. FIG. 1 of that patent proposes an arrangement in which two components are disposed in surrounding relation to the heart and function to compress the heart therebetween to assist ventricular output thereof. The two components are furnished with electromagnetic induction circuitry, numerous pole elements, and are secured to one another by a mechanical hinge. It can be appreciated that the device is quite cumbersome, difficult to implant, and has achieved little if any acceptance.

FIG. 4 of the '617 patent illustrates an alternate arrangement in which a compressor element is provided posteriorly to the heart and is movable to compress the heart against the rib cage. This embodiment is somewhat more practical, but nevertheless problematic in a number of respects. For example, no means are provided for evaluating the amount of compressive resistance or intra-cardiac pressure of the heart during compression thereof. As a result, the compressor element may either apply insufficient compressive force to the heart, thereby resulting in ineffective ventricular assist, or apply excessive compressive force, thereby damaging the heart. Additionally, providing a compressor element posteriorly to the heart requires complex surgery in which the entire chest cavity must be opened. Moreover, such placement of the compressor element is largely impractical since the aorta, esophagus and spine are all disposed in close proximity to the posterior portion of the heart and leave little room for insertion of any type of assist device.

SUMMARY OF THE INVENTION

It is therefore an object of the present invention to provide a cardiac assist device which overcomes the aforementioned problems. To remedy the potential problems associated with controlling the amount of compressive force applied to the heart, the device comprises a magnetic mat which can be mounted inside the human body adjacent the heart. The mat is movable into compressive relation with the heart in response to application of an electromagnetic field. The device includes an electromagnetic assembly which is operable to alternately generate and discontinue a magnetic field so that the mat alternately moves into and out of compressive relation with the heart. A transducer is provided for evaluating the compressive resistance of the heart during movement of the mat into compressive relation therewith. The transducer generates a signal to a control circuit which controls the intensity of the electromagnetic field applied by the electromagnetic assembly. Thus, the degree to which the mat compresses the heart can be effectively controlled.

In an alternate embodiment, the transducer measures intra-cardiac pressure within the heart and generates a signal as a function thereof. The control circuit is responsive to such signal, and controls the intensity of the electromagnetic field and the degree to which the mat compresses the heart as a function of the intra-cardiac pressure within the heart.

It is also an object of the invention to remedy the problem associated with placement of a cardiac assist compressor element posteriorly to the heart. To accomplish this object, the magnetic mat is secured to the rib cage by a flexible support anteriorly to the heart. The mat is movable to compress the heart against the vertebral body in response to application of a predetermined electromagnetic field, and is movable out of compressive relation to permit the heart to relax when application of the predetermined electromagnetic field is discontinued.

It is a further object of the present invention to provide a method for assisting right and left ventricular output in a human heart by compressing the heart against the vertebral body. This method comprises the steps of generating an electrocardiogram as a function of electrical activity of the heart; generating an electromagnetic field with an electromagnetic assembly as a function of said electrocardiogram; and moving a magnetic mat towards the vertebral body to compress the heart therebetween in response to application of said electromagnetic field thereto.

Other objects and advantages of the invention will be apparent from the following description, the accompanying drawings, and the appended claims.

DETAILED DESCRIPTION OF THE PRESENTLY PREFERRED EXEMPLARY EMBODIMENTS

Figure 1:
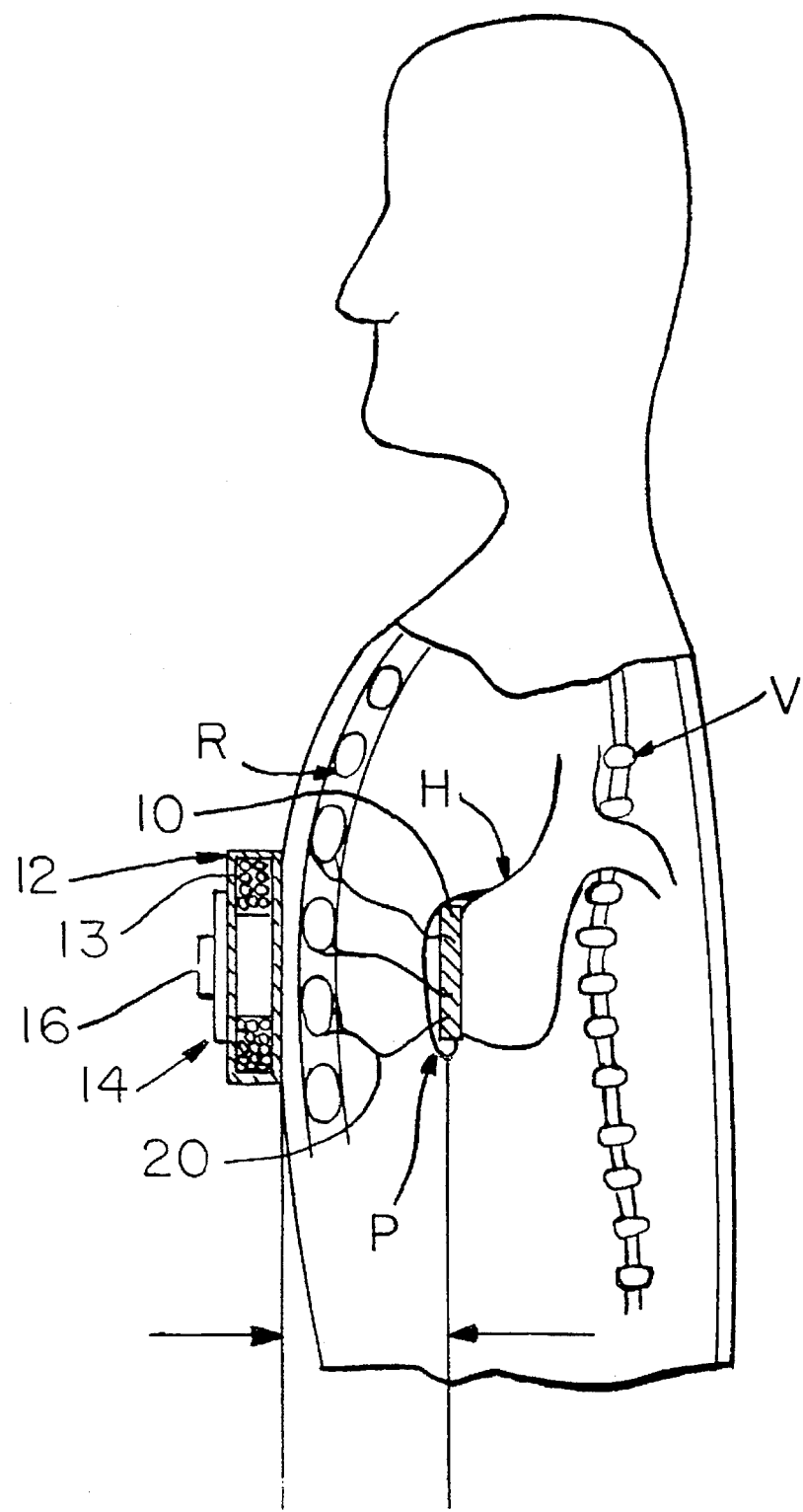
FIG. 1 is a side sectional view of the cardiac assist device of the present invention shown inside the human body in non-compressive relation with the heart.

FIG. 1 is a side sectional view taken through the human body and the cardiac assist device of the present invention, which is shown in non-compressive relation with the human heart.

In the illustrated embodiment, the device includes a magnetic mat 10 which is adapted to be mounted inside the human body inside of the rib cage R, adjacent the heart H. Preferably, mat 10 is a permanent magnet made from a flexible ferro-magnetic material, such as samarium cobalt or neodymium iron. It can be appreciated, however, that the mat may comprise other materials (such as a superconductive material) so long as the mat is sufficiently responsive to application of an electromagnetic field to compress the heart in accordance with the principles of the present invention. Regardless of the material used, however, the exterior surface of the mat should be chemically inert, and not immunogenic, so that it does not react with blood, tissue, or organs. If necessary, the mat may be coated or surrounded by an inert substance such as polyvinyl chloride or polytetrafluoroethylene (PTFE).

The mat is supported within the body, preferably in the space between the anterior aspect of the heart H and the posterior aspect of the pericardium P, although, as will be described later, the mat can also be positioned anteriorly to both the heart and pericardium. Preferably the mat support comprises a plurality of heavy mono-filament threads 20 each having one end secured to the mat and another end secured to the rib cage R (or sternum). The threads are flexible to permit movement of the mat, and should be sufficiently strong to withstand continued flexing without breakage. Where the mat is disposed between the heart and pericardium, the threads 20 are sutured through the pericardium. It can be appreciated that many alternatives to the mono-filament threads can be used to support the mat, as long as such alternatives maintain the mat in movably supported relation, anteriorly and proximate to the heart.

Figure 2:
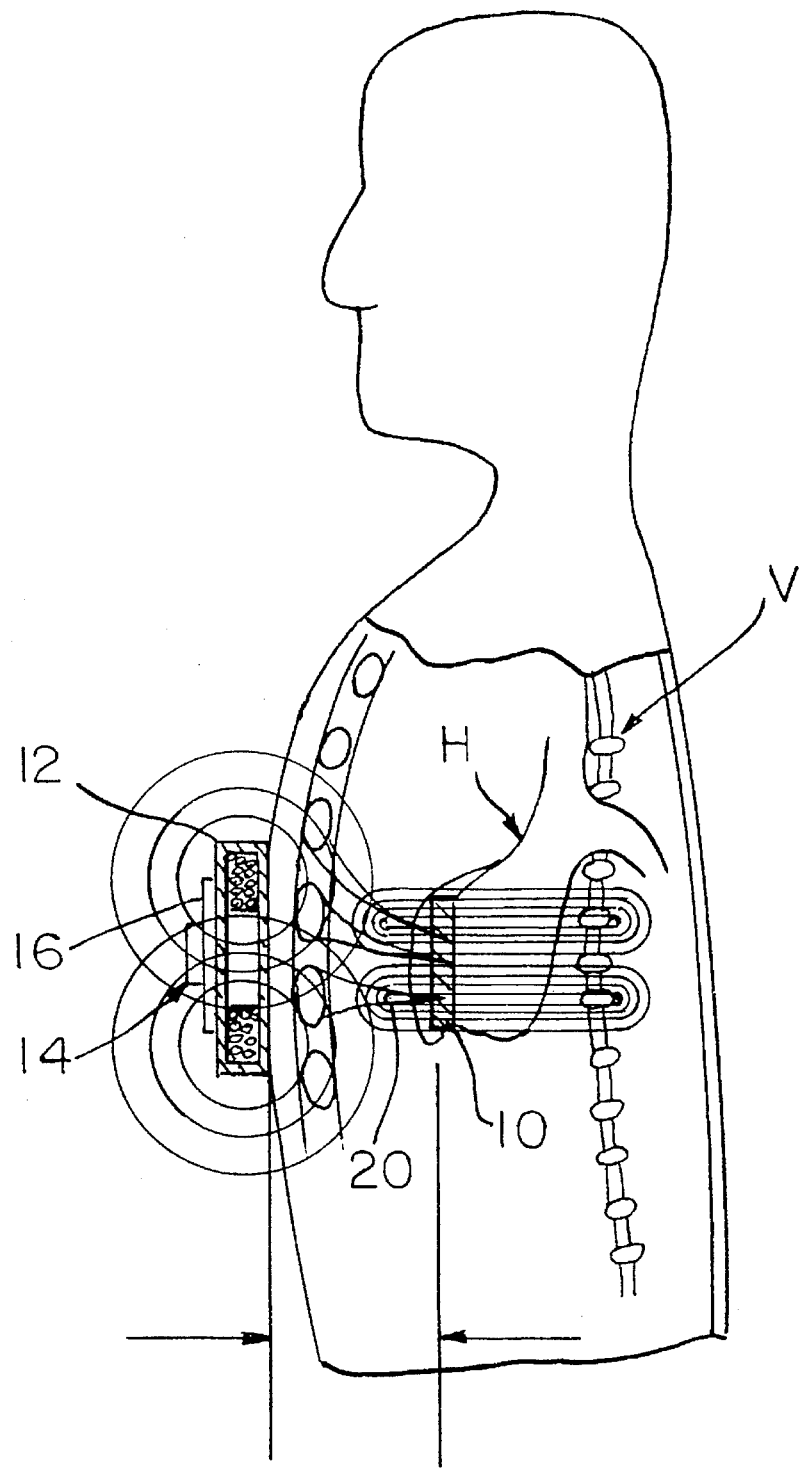
FIG. 2 is a side sectional view of the cardiac assist device of the present invention shown inside the human body in compressive relation with the heart.

An electromagnetic assembly 12 is adapted to be mounted externally on the human body, preferably on the chest, in functionally cooperative relation with respect to the mat 10. The electromagnetic assembly 12 includes inductive coils 13 through which a current is generated (preferably by a D.C. battery, not shown) to produce an electromagnetic field, which repels the mat into compressive relation with the heart, as shown in FIG. 2. More particularly, electromagnetic assembly 12 alternately generates and discontinues the electromagnetic field to alternately compress the heart against vertebral body V (e.g., the spine) and then permit the heart to relax, thereby assisting the mechanical pumping function of the heart. The magnitude of the force produced will be proportionally dependent on the mat's magnetic field strength, the amount of current travelling through the electromagnetic assembly 12, and the number of current-turns in the electromagnetic assembly 12, but inversely proportional to the distance between the electromagnetic assembly and the mat.

Figure 3:
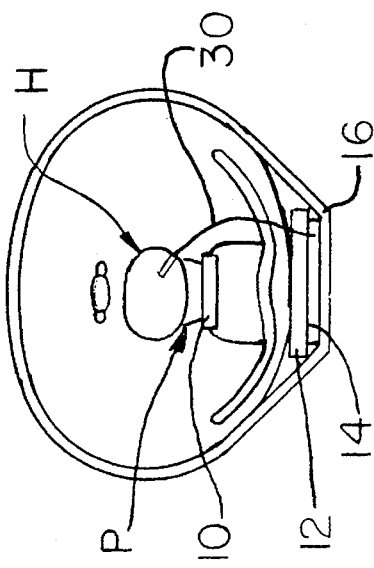
FIG. 3 is a top sectional view showing the cardiac assist device of the present invention inside the human body.

A transducer 14 (preferably a load cell, force gauge type, made from piezo AC material) is secured to the electromagnetic assembly 12 on the side opposite the chest by a preferably rigid harness 16. The harness is disposed in surrounding relation to the human torso as shown in FIG. 3, which is a top sectional view through the torso. The harness 16 may include shoulder straps to prevent vertical movement of the electromagnetic assembly 12 when an individual is in the upright position.

In FIG. 3, the mat as shown is positioned anteriorly to both the heart and pericardium. It can be appreciated, however, that it is more preferable to position the mat in the natural space between the heart and pericardium to enable the mat to more effectively compress the heart by being in direct contact therewith. In addition, placement of the mat anteriorly to the pericardium is more difficult since a significant amount of body tissue between the pericardium and sternum must be removed to enable such placement.

Figure 4:
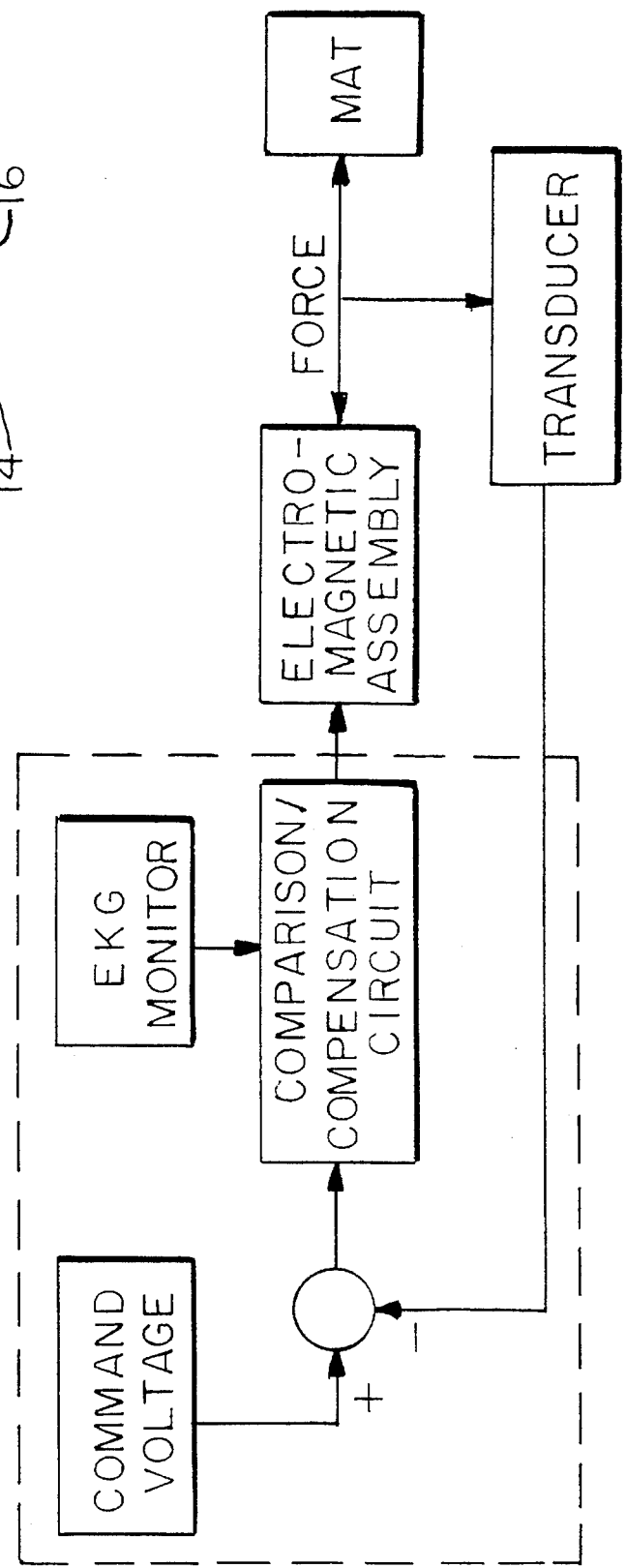
FIG. 4 is a block diagram schematically showing the interrelation of various components of the present invention.

As shown in FIG. 4, the transducer 14 forms part of an electronic feedback/control loop, and functions to evaluate the compressive resistance of the heart during movement of the mat into compressive relation with the heart. More specifically, when the electromagnetic assembly 12 generates an electromagnetic field to repel mat 10, an equal and opposite force is applied to the electromagnetic assembly, thus repelling the assembly away from the chest. It can be appreciated that when such an electromagnetic field is generated, pressure transducer 14 is compressed between the assembly 12 and harness 16 (e.g., see FIG. 2). The transducer 14 senses the compressive pressure or force applied thereto and outputs a voltage proportional to such force or pressure. A control circuit 22 receives the signal generated by the transducer and controls the intensity of said electromagnetic field generated by the electromagnetic assembly as a function of that signal. As a result, the control circuit effectively controls the degree to which the mat compresses the heart.

More specifically, control circuit 22 includes a compensation/comparison circuit 26 (or "compensation circuit") which compares the voltage generated by transducer 14 to a command voltage generated by command voltage generator 24. The command voltage corresponds to a predetermined voltage which represents the ideal amount of force required to compress the heart. The compensation/comparison circuit 26 measures the difference between the voltage generated by the pressure transducer 14 and the command voltage, and then digitally compensates for such difference so that an appropriate amount of current is sent through the coils in the electromagnetic assembly 12. For example, if the voltage generated by transducer 14 is less than the command voltage, the compensation circuit 26 will ramp up the current sent through coils 13 and thereby increase the intensity of the magnetic field applied by electromagnetic assembly 12. In contrast, if the voltage generated by transducer 14 is less than the command voltage, the compensation circuit will decrease the amount of current through coils 13 and thereby decrease the intensity of the magnetic field applied by the electromagnetic assembly 12. Thus, the intensity or magnitude of the electromagnetic field generated by the electromagnetic assembly is controlled so that the compressive force applied by the mat 10 to the heart remains within a predetermined range with each compressive stroke.

The predetermined amount of force to be applied to the heart in order to obtain the desired cardiac output is determined experimentally during an initial procedure wherein a catheter, such as the Swan-Ganz catheter, is placed in the heart to monitor intra-ventricular pressures. This type of catheter is also capable of measuring actual cardiac output. The cardiac output and intra-cardiac pressure are correlated with the voltages generated by pressure transducer 14, and after several days of experimentation, the Swan-Ganz catheter may be removed. The pressure transducer 14 thereafter generates a voltage as a function of the compressive resistance of the heart, which in turn is a function of either the intra-cardiac pressure or output of the heart.

It can be appreciated that the Swan-Ganz catheter may be kept within the heart and utilized as a transducer in lieu of transducer 14. Such an arrangement is shown in FIG. 3, wherein a Swan-Ganz catheter 30 is in place. It is advantageous, however, to remove the Swan-Ganz catheter since use thereof requires the provision of wires extending through the human flesh from the catheter to the electromagnetic assembly 12 and control circuit. This can be quite uncomfortable for the subject.

While the magnitude of the electromagnetic field generated by electromagnetic assembly 12 is controlled by the control circuit 22 together with the pressure transducer 14, it can be appreciated that the frequency of the electromagnetic field must coincide with the natural contractions of the heart. This is accomplished by use of an electrocardiogram (EKG) 28 monitor integrated into the control circuit. The EKG monitor measures the electrical activity of the heart and, together with the rest of the control circuit, functions to synchronize the electromagnetic field generated by the electromagnetic assembly with the QRS spike of the electrocardiogram. This technique of adjusting the rate at which the mat compresses the heart is similar to that used in intra-aortic balloon pumps, and is conventional in this field of technology.

The preferred procedure for inserting the mat 10 into the human body in cooperative relation the heart will now be described. The heavy mono-filament threads 20 each have one end thereof secured to the peripheral edges of two opposite sides of the mat, which preferably has a substantially rectangular or oval shape. An incision is made immediately below the breastbone using the sub-xiphoid approach, and the threads are then sutured to the rib cage and/or sternum by use of curved trochar sheath. The sutures are passed anteriorly to the epicardium, but posterior to the anterior aspect of the pericardium, and exit intercostally lateral to the sternum. Enough slack should be left in the mono-filament sutures to permit movement of the mat 10 away from the electromagnetic assembly 12 into compressive relation with the heart upon application of the electromagnetic field.

While the assembly of the present invention can be used to temporarily assist the mechanical pumping function of the heart (for example, in patients waiting for cardiac transplants, patients with septic shock whose heart is disabled until the endotoxin and/or cardiodepressant factor has been cleared, and patients in cardiogenic shock due to acute ischemia), the invention can also be used as permanent cardiac assist device as it is intended to function for a great number of years with little or no maintenance.

The assembly in accordance with the principles of the present invention has additional benefits in that it alleviates problems associated with an over-distended, dilated myocardium as the repeated application of compressive force on the heart tends to decrease the heart size (or at least inhibit growth thereof). This is beneficial to electrical conduction and thus mechanical performance of the heart.

It will be appreciated that the objects of this invention have been fully and effectively accomplished. It will be realized, however, that the foregoing preferred specific embodiments have been shown and described for the purpose of this invention and is subject to change without departure from such principles. Therefore, this invention includes all modifications encompassed within a spirit and scope of the following claims.

What is claimed is:

1. An electromagnetic cardiac assembly adapted to assist ventricular output in a human heart comprising:

a magnetic mat adapted for mounting inside a human body adjacent the heart, said mat being made from a material responsive to application of an electromagnetic field so as to be movable into compressive relation with the heart in response to application of the electromagnetic field thereto and movable out of said compressive relation to permit the heart to relax when application of said electromagnetic field is discontinued;

electromagnetic assembly means adapted for mounting on the human body in functionally cooperative relation with respect to said mat, and for alternately generating and discontinuing said electromagnetic field so that said mat alternately moves into and out of said compressive relation with the heart;

a transducer for evaluating compressive resistance of the heart during movement of said mat into compressive relation with the heart and for generating an electrical signal as a function of said compressive resistance of the heart; and control circuit means for receiving said signal generated by said transducer and for controlling an intensity level of the electromagnetic field generated by said electromagnetic assembly means as a function of said signal to thereby control a degree to which said mat compresses the heart.

2. The electromagnetic cardiac assembly according to claim 1, further comprising a flexible support adapted to secure the mat to a human rib cage in movable relation between the heart and the rib cage.

3. The electromagnetic cardiac assembly according to claim 2, wherein said flexible support comprises heavy mono-filament threads, and wherein said mat is adapted to be disposed between an anterior aspect of the heart and a posterior aspect of the pericardium, said threads extending from the mat through the pericardium to the rib cage.

4. The electromagnetic cardiac assembly according to claim 1, wherein said magnetic mat is substantially flexible so as to be adapted to conform to the shape of the heart and comprises a permanent magnet surrounded by an insulative layer, and wherein said electromagnetic field generated by said electromagnetic assembly means magnetically repels the mat away therefrom into said compressive relation with the heart.

5. The electromagnetic cardiac assembly according to claim 1, wherein said control circuit means comprises an electrocardiogram monitor for generating signals as a function of electrical activity of the heart, said signals being used to determine a rate at which said electromagnetic assembly means alternately generates and discontinues application of said electromagnetic field so that said mat alternately moves into and out of said compressive relation with the heart as a function of the electrical activity of the heart.

6. The electromagnetic cardiac assembly according to claim 1, further comprising a harness for mounting said electromagnetic assembly means on the human body.

7. The electromagnetic cardiac assembly according to claim 6, wherein said transducer is compressed between said harness and said electromagnetic assembly means, and wherein compressive force applied to said transducer enables said transducer to generate said signal as a function of the compressive resistance of the heart.

8. The electromagnetic cardiac assembly according to claim 1, wherein said electromagnetic assembly means comprises inductive coils, and wherein said control circuit means controls an amount of current which travels through said coils, the amount of current which travels through said coils being proportional to an intensity level of the electromagnetic field generated by said electromagnetic assembly means.

9. The electromagnetic cardiac assembly according to claim 7, wherein said transducer comprises a load cell force gauge.

10. The electromagnetic cardiac assembly according to claim 8, wherein said signal generated by said transducer is a voltage proportional to the compressive resistance of the heart, and wherein the control circuit means comprises a compensation circuit for comparing a command voltage to said proportional voltage and for adjusting the amount of current which travels through said coils as a function of a difference between said command and proportional voltages.

11. An electromagnetic cardiac assembly for assisting ventricular output in a human heart comprising:

a magnetic mat adapted for mounting inside a human body adjacent the heart, said mat comprising a material responsive to application of an electromagnetic field so as to be movable into compressive relation with the heart in response to application of the electromagnetic field and movable out of said compressive relation to permit the heart to relax when application of said electromagnetic field is discontinued;

electromagnetic assembly means adapted for mounting on the human body in functionally cooperative relation with respect to said mat, and for alternately generating and discontinuing said electromagnetic field so that said mat alternately moves into and out of said compressive relation with the heart;

a pressure transducer for measuring intra-cardiac pressure within the heart and for generating a signal as a function of said intra-cardiac pressure; and control circuit means for receiving said signal generated by said transducer and for controlling an intensity of said electromagnetic field generated by said electromagnetic assembly means as a function of said signal to thereby control a degree to which the mat compresses the heart as a function of the intra-cardiac pressure within the heart.

12. The electromagnetic cardiac assembly according to claim 11, further comprising a flexible support adapted to secure the mat to a human rib cage in movable relation between the heart and the rib cage.

13. The electromagnetic cardiac assembly according to claim 12, wherein said flexible support comprises heavy mono-filament threads, and wherein said mat is adapted to be disposed between an anterior aspect of the heart and a posterior aspect of the pericardium, said threads extending from the mat through the pericardium to the rib cage.

14. The electromagnetic cardiac assembly according to claim 11, wherein said magnetic mat comprises a permanent magnet, and wherein said electromagnetic field generated by said electromagnetic assembly means magnetically repels the mat away therefrom into said compressive relation with the heart.

15. The electromagnetic cardiac assembly according to claim 11, wherein said control circuit means comprises an electrocardiogram monitor for generating signals as a function of electrical activity of the heart, said signals being used to determine a rate at which said electromagnetic assembly means alternately generates and discontinues application of said electromagnetic field so that said mat alternately moves into and out of said compressive relation with the heart as a function of the human heart rate.

16. The electromagnetic cardiac assembly according to claim 11, wherein said pressure transducer comprises a Swan-Ganz catheter.

17. The electromagnetic cardiac assembly according to claim 11, wherein said electromagnetic assembly means comprises inductive coils, and wherein said control circuit means controls an amount of current which travels through said coils, the amount of current which travels through said coils being proportional to the intensity level of the electromagnetic field generated by said electromagnetic assembly means.

18. The electromagnetic cardiac assembly according to claim 17, wherein said signal generated by said pressure transducer is a voltage proportional to said intra-cardiac pressure, and wherein the control circuit means comprises a compensation circuit for comparing a command voltage to said proportional voltage and for adjusting the amount of current which travels through said coils as a function of a difference between said command and proportional voltages.

19. A method for assisting ventricular output in a human heart by compressing the heart against a vertebral body comprising the steps of:

detecting an electrocardiogram as a function of electrical activity of the heart;

generating an electromagnetic field with an electromagnetic assembly as a function of said electrocardiogram; and moving a magnetic mat disposed anteriorly to the heart towards the vertebral body so as to force the heart against the vertebral body and thereby compress the heart between the magnetic mat and the vertebral body in response to application of said electromagnetic field to said mat.

* * * * *